United States Patent
Brouet

(10) Patent No.: US 11,141,743 B2
(45) Date of Patent: Oct. 12, 2021

(54) DEVICE FOR DISPENSING FLUID PRODUCT

(71) Applicant: APTAR FRANCE SAS, Le Neubourg (FR)

(72) Inventor: Guillaume Brouet, Rouen (FR)

(73) Assignee: APTAR FRANCE SAS, Le Neubourg (FR)

(*) Notice: Subject to any disclaimer, the term of this patent is extended or adjusted under 35 U.S.C. 154(b) by 0 days.

(21) Appl. No.: 16/627,437

(22) PCT Filed: Jul. 3, 2018

(86) PCT No.: PCT/FR2018/051641
§ 371 (c)(1),
(2) Date: Dec. 30, 2019

(87) PCT Pub. No.: WO2019/008260
PCT Pub. Date: Jan. 10, 2019

(65) Prior Publication Data
US 2020/0254465 A1 Aug. 13, 2020

(30) Foreign Application Priority Data
Jul. 6, 2017 (FR) ...................................... 1756365

(51) Int. Cl.
*B05B 1/28* (2006.01)
*A61M 15/00* (2006.01)
*A61M 15/08* (2006.01)

(52) U.S. Cl.
CPC ............. *B05B 1/28* (2013.01); *A61M 15/009* (2013.01); *A61M 15/08* (2013.01); *A61M 2205/7527* (2013.01)

(58) Field of Classification Search
CPC ............ A61M 11/007; A61M 15/0036; A61M 15/009; A61M 15/08; A61M 2205/7527;
(Continued)

(56) References Cited

U.S. PATENT DOCUMENTS 5,307,953 A * 5/1994 Regan ............... A61M 15/0028
222/82
5,813,570 A * 9/1998 Fuchs ..................... B05B 11/02
222/82

(Continued)

FOREIGN PATENT DOCUMENTS

DE 14 25 861 A1 11/1968
WO 97/29028 A1 8/1997
WO 2014/147329 A1 9/2014

OTHER PUBLICATIONS

International Preliminary Report on Patentability with a Translation of Written Opinion in International Application No. PCT/FR2018/051641, dated Jan. 16, 2020.
(Continued)

*Primary Examiner* — Vishal Pancholi
*Assistant Examiner* — Bob Zadeh
(74) *Attorney, Agent, or Firm* — Sughrue Mion, PLLC

(57) ABSTRACT

A fluid dispenser device comprising: a reservoir (10) containing fluid; a dispenser head (20) that is provided with a dispenser orifice (21); dispenser means (25) for dispensing at least a fraction of said fluid through said dispenser orifice (21); and passage means (40) for connecting said reservoir (10) to said dispenser orifice (21) on actuation of said dispenser means (25), said device further comprising at least one porous insert (50) that is made out of porous material so as to suck up, in particular by capillarity, and to trap, at least in part, any residual fluid after actuation; said reservoir (10) including a stopper (25) that closes said reservoir (10) in leaktight manner before actuation.

12 Claims, 2 Drawing Sheets

(58) Field of Classification Search
CPC .. B05B 1/28; B05B 11/02; B67B 7/24; B67B 7/26; B65D 5/747
See application file for complete search history.

(56) References Cited

U.S. PATENT DOCUMENTS

| | | | | |
|---|---|---|---|---|
| 6,626,379 | B1* | 9/2003 | Ritsche | B05B 11/0078 239/303 |
| 6,708,846 | B1* | 3/2004 | Fuchs | A61M 11/06 222/82 |
| 7,299,949 | B2* | 11/2007 | Greiner-Perth | B05B 11/02 222/153.13 |
| 9,592,934 | B2 | 3/2017 | Painchaud et al. | |
| 2005/0023295 | A1* | 2/2005 | Tempfli | A61M 15/0036 222/135 |
| 2007/0093765 | A1* | 4/2007 | Kawashiro | B65D 47/18 604/295 |
| 2008/0210229 | A1 | 9/2008 | Corbacho | |
| 2012/0041372 | A1* | 2/2012 | Kiehne | A61M 25/0631 604/164.12 |
| 2017/0129662 | A1* | 5/2017 | Decock | B65D 47/40 |
| 2020/0254465 | A1* | 8/2020 | Brouet | A61M 11/007 |

OTHER PUBLICATIONS

International Search Report for PCT/FR2018/051641 dated Oct. 10, 2018 [PCT/ISA/210].

* cited by examiner

DEVICE FOR DISPENSING FLUID PRODUCT

CROSS REFERENCE TO RELATED APPLICATIONS

This application is a National Stage of International Application No. PCT/FR2018/051641 filed Jul. 3, 2018, claiming priority based on French Patent Application No. 1756365 filed Jul. 6, 2017.

The present invention relates to a fluid dispenser device.

More particularly, the present invention relates to a fluid dispenser device for dispensing a pharmaceutical fluid to a user, e.g. by means of a nasal spray. However, the present invention also applies to dispenser devices for dispensing fragrance or cosmetics. In that type of device, the fluid, which is generally liquid, is dispensed or sprayed through a dispenser orifice while the device is being actuated manually. After each actuation, it can happen that some fluid remains in the dispenser orifice and inside the channels and passages that connect the reservoir to said dispenser orifice. In the pharmaceutical field in particular, this can pose problems. Firstly, such residues may dry out and block the orifice and/or the fluid passages and thus prevent the device from being actuated subsequently. Secondly, such residual volumes of active agents may be a source of contamination. In particular, in devices of the dual-dose type, i.e. devices adapted to dispense two doses, if the second dose is not dispensed immediately after the first, there is a risk of the second dose being contaminated. Furthermore, for highly active substances, such as Fentanyl for example, which is an agent used for treating pain and is one hundred times more powerful than morphine, it is necessary to avoid any risk of a third party using any residual volume, since the consequences would be dramatic. In a hospital context, use is managed by professionals, but there are now a large number of substances of this type that are used directly in a patient's home, resulting in greater exposure to risk. The regulatory authorities are very sensitive to this aspect, and invariably require laboratories to put means into place for reducing access to any residual volume.

Documents U.S. Pat. No. 9,592,934, DE 1 425 861, and US2017/129662 describe prior-art devices.

An object of the present invention is to provide a fluid dispenser device that does not have the above-mentioned drawbacks.

More particularly, an object of the present invention is to provide a fluid dispenser device that avoids or limits any risk of blocking the device, and any risk of contaminating the fluid.

Another object of the present invention is to provide such a device that prevents or limits access to any residual volumes of fluid after use.

Another object of the present invention is to provide such a device that is simple and inexpensive to manufacture and to assemble.

The present invention thus provides a fluid dispenser device comprising: a reservoir containing fluid; a dispenser head that is provided with a dispenser orifice; dispenser means for dispensing at least a fraction of said fluid through said dispenser orifice; and passage means for connecting said reservoir to said dispenser orifice on actuation of said dispenser means, said device further comprising at least one porous insert that is made out of porous material so as to suck up, in particular by capillarity, and to trap, at least in part, any residual fluid after actuation; said reservoir including a stopper that closes said reservoir in leaktight manner before actuation.

Advantageously, said passage means include a needle that is adapted to pierce said stopper during actuation.

Advantageously, said needle is stationary relative to said dispenser orifice.

Advantageously, said porous insert is made out of porous hydrophilic polymer.

In a first advantageous embodiment, said porous insert is arranged, at least in part, around said passage means.

Advantageously, after actuation, said porous insert extends, at least in part, into said reservoir.

Advantageously, a proximal rigid insert is arranged downstream from said porous insert.

Advantageously, said proximal rigid insert defines a spray profile directly upstream from said dispenser orifice.

Advantageously, a distal rigid insert is arranged upstream from said porous insert.

Advantageously, said porous insert is arranged axially between said proximal rigid insert and said distal rigid insert.

In a second advantageous embodiment, said porous insert is arranged in said reservoir.

Advantageously, said reservoir contains a second stopper that separates said porous insert from the fluid contained in said reservoir.

Advantageously, at the end of actuation, said needle pierces said second stopper so as to connect said porous insert to said passage means.

These and other characteristics and advantages of the present invention appear more clearly from the following detailed description, given by way of non-limiting examples, and with reference to the accompanying drawings, and in which.

The terms "proximal" and "distal" are relative to the dispenser orifice. The terms "axial" and "radial" refer to the longitudinal central axis A shown in FIGS. 1 and 5. The terms "upstream" and "downstream" refer to the direction of flow of the fluid during actuation.

Figure 1:
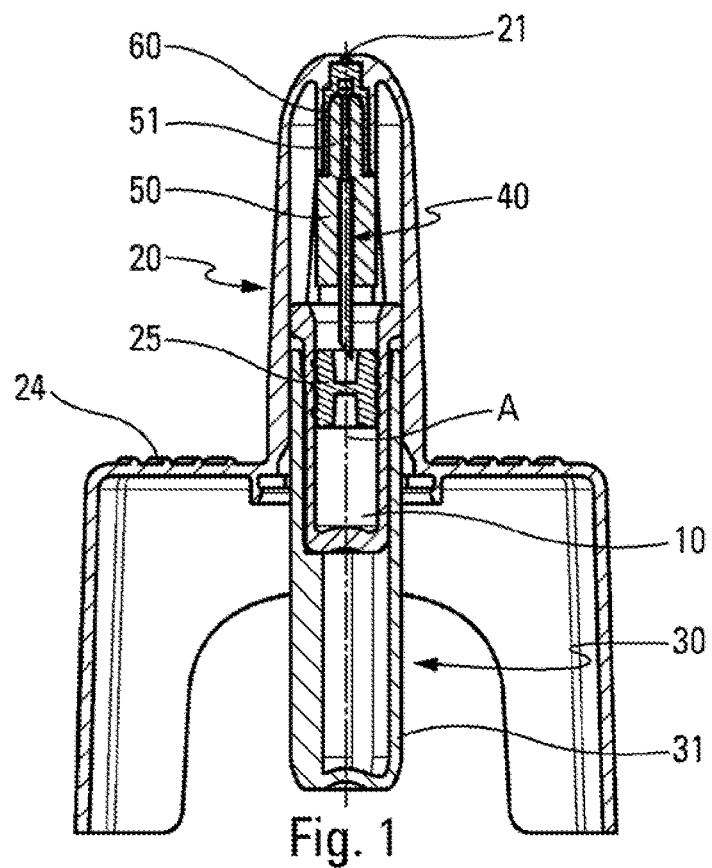
FIG. 1 is a diagrammatic section view of a fluid dispenser device in a first advantageous embodiment of the present invention, shown in its rest position before actuation.
Figure 2:
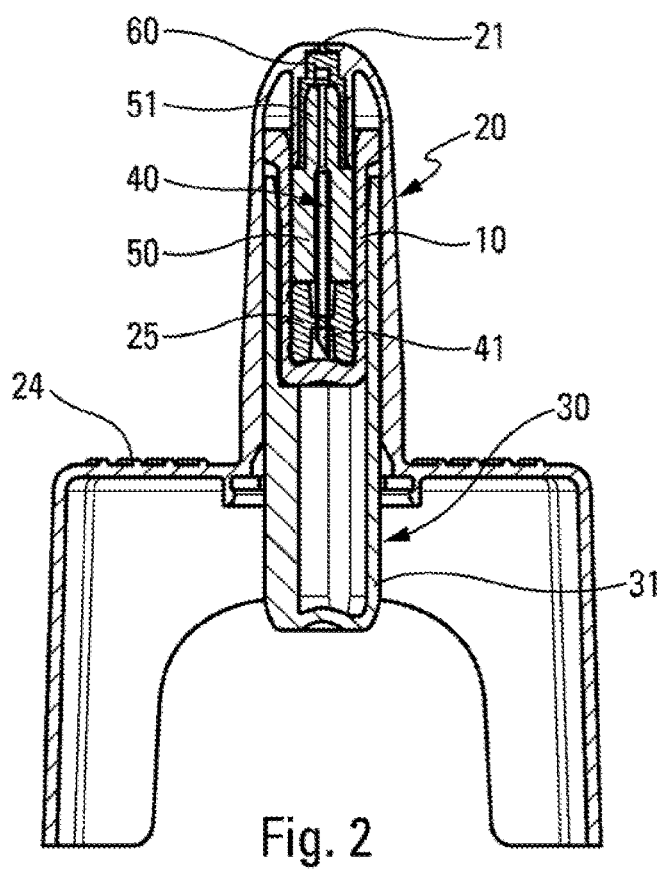
FIG. 2 is a view similar to the view in FIG. 1, showing the device after actuation.

FIGS. 1 and 2 show a first advantageous embodiment of the present invention. In this first embodiment, a reservoir 10 containing fluid to be dispensed, typically a liquid, is arranged inside a body that forms a dispenser head 20. The dispenser head 20 includes a dispenser orifice 21 that is oriented axially in the embodiment in the figures, but that could be oriented in some other way, e.g. radially. The dispenser orifice 21 serves to dispense a dose of fluid out from said dispenser head 20 while the device is being actuated by a user, such dispensing being performed by dispenser means.

In this embodiment, the reservoir 10 is formed by a body that is hollow and blind, including a single opening that is closed by a stopper 25 and containing a single dose of fluid to be dispensed during a single actuation of the device. It should be observed that the present invention could also be adapted to devices of the dual-dose type, containing two doses of fluid to be dispensed during two successive actuations of the device.

The dispenser head 20 includes passage means 40 that, during actuation, connect the reservoir 10 to the dispenser orifice 21. The passage means 40 advantageously include a needle 41 that is adapted to pierce the stopper 25 at the time of actuation. The needle 41 is hollow and may be formed in conventional manner. Preferably, the needle 41 is stationary relative to the dispenser head 20, and in particular relative to the dispenser orifice 21. In a variant, the needle could be movable relative to said dispenser head 20.

Other passage means may be envisaged, e.g. passage means without a needle, as described in document WO 97/29028, for example.

Actuator means 30 are provided so as to make it possible to actuate the device. Specifically, the actuator means 30 comprise an actuator body 31 that is movable relative to the dispenser head 20, said actuator body 31 co-operating with said reservoir 10 so as to move it axially relative to the dispenser head 20 and thus relative to the needle 41, towards the dispenser orifice 21.

In the invention, the device includes an insert 50 that is made out of porous material so as to suck up, by capillarity, and to trap, at least in part, any residual fluid after the device has been actuated, in particular in said passage means 40 and/or in said dispenser orifice 21.

In the first embodiment in FIGS. 1 and 2, said porous insert 50 is arranged, at least in part, around said passage means 40.

In this embodiment, the insert 50 extends around the needle 41, and continues towards the dispenser orifice 21. As can be seen in FIG. 2, at the end of actuation, said insert 50 comes into contact with the stopper 25 in the reservoir 10.

Preferably, a proximal rigid insert 60 is provided downstream from said porous insert 50, so as to define a spray profile directly upstream from the dispenser orifice 21, in order to guarantee that the fluid is properly sprayed while it is being dispensed. In the embodiment shown in FIGS. 1 and 2, said proximal rigid insert 60 is arranged, in part, around a proximal small-diameter portion 51 of said porous insert 50. In particular, the needle 41 may extend into said porous insert 50 until it reaches said small-diameter portion 51. In this configuration, the porous insert 50 is in contact with the fluid to be dispensed only at said small-diameter portion 51.

Figure 3:
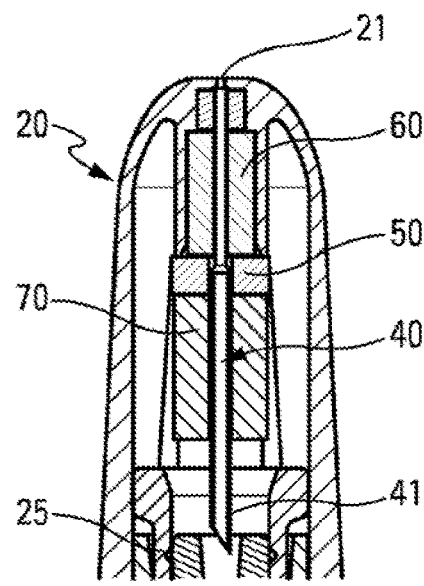
FIG. 3 is a view of a detail of a variant embodiment of the device in FIGS. 1 and 2, shown in its rest position before actuation.

FIG. 3 shows a variant of the first embodiment, in which, in addition to said proximal rigid insert 60, a distal rigid insert 70 is provided, arranged upstream from said porous insert 50. This embodiment enables the needle 41 to be fastened better to the distal rigid insert 70, reducing the size of said porous insert 50, which nevertheless remains sufficient to absorb the volume of any residual fluid after actuation. Advantageously, said porous insert 50 is arranged axially between said proximal and distal rigid inserts 60, 70.

Figure 4:
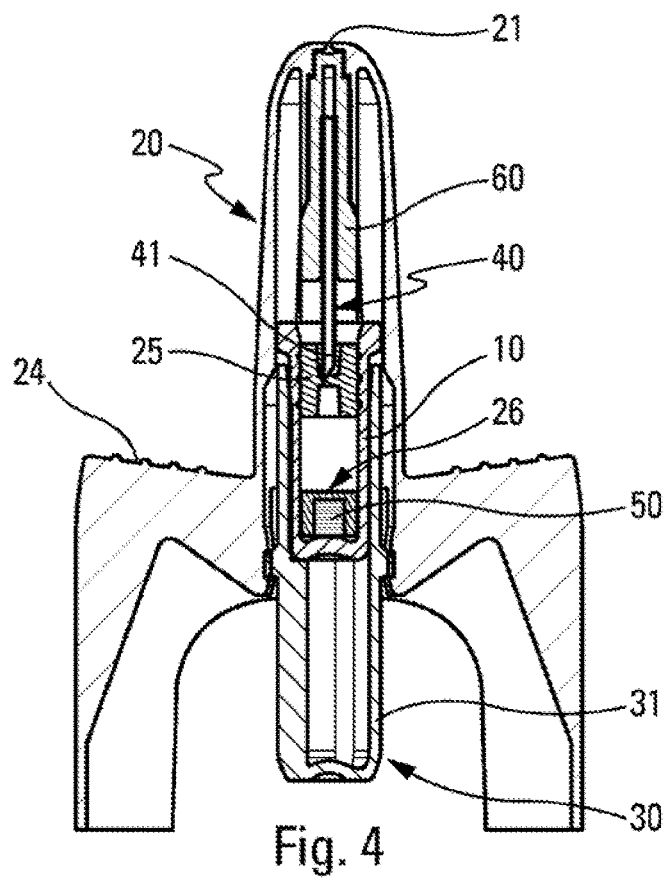
FIG. 4 is a diagrammatic section view of a fluid dispenser device in a second advantageous embodiment of the present invention, shown in its rest position before actuation.
Figure 5:
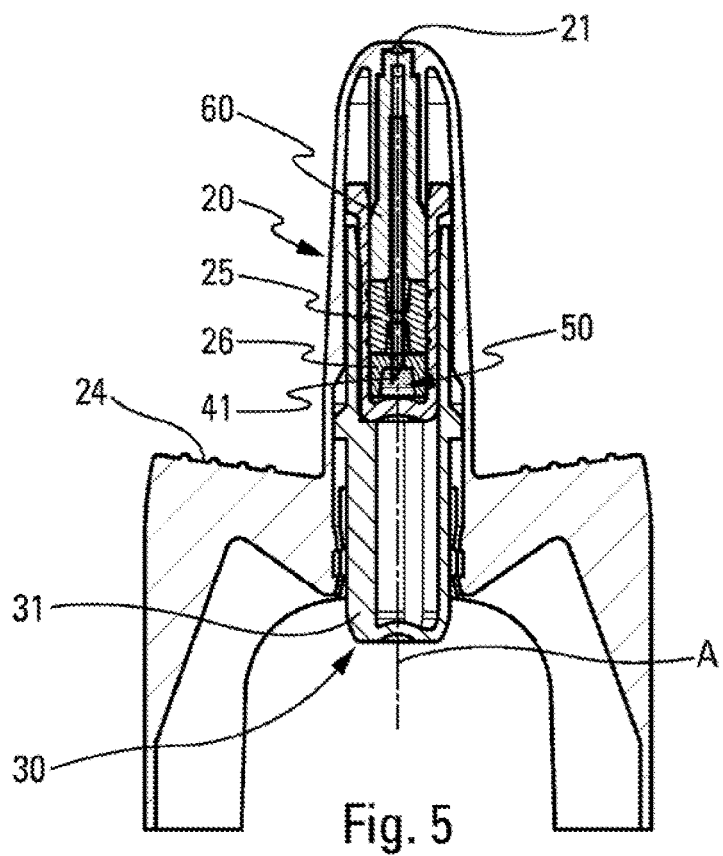
FIG. 5 is a view similar to the view in FIG. 4, showing the device after actuation.

FIGS. 4 and 5 show a second embodiment in which said porous insert 50 is arranged at the bottom of the reservoir 10. A second stopper 26 separates said porous insert 50 from the fluid contained in the reservoir 10. As can be seen in FIG. 5, at the end of dispensing the fluid, the needle 41 comes to pierce the second stopper 26 so as to connect said porous insert to the passage means 40. This enables said porous insert 50 to suck up, in particular by capillarity, any residual fluid, at least in part, after actuation.

Optionally, the two above-described embodiments could be combined, and two porous inserts could be provided, one around the passage means 40, and the other at the bottom of the reservoir 10.

Advantageously, said porous insert 50 is made out of porous hydrophilic polymer, such as Porex®. Other equivalent porous materials may also be envisaged.

Operation of the device shown in the figures is described in detail below.

In conventional manner, in the device shown in the figures, the user places two fingers on radial bearing surfaces 24 that are formed on the dispenser head 20, and presses with the thumb on the distal axial bottom wall of said actuator body 31. During such actuation, the reservoir 10 is thus pushed axially towards the dispenser orifice 21, so that the needle 41 pierces the stopper 25. The contents of the reservoir 10 are thus connected to the dispenser orifice 21, and the user pressing on the actuator body 31 moves the stopper 25 in the reservoir 10 so as to dispense the fluid. The stopper 25 thus acts as a piston, forcing the fluid out from said reservoir 10, through the needle 41. In this embodiment, the stopper 25 thus forms the dispenser means that, during actuation, dispense the fluid through the dispenser orifice. At the end of dispensing, any residual fluid that might remain inside the device, in said passage means 40 and/or in said dispenser orifice 21, is sucked up, at least in part, by said porous insert 50, preventing access to this trapped volume of residual fluid.

In another embodiment that is not shown in the drawings, the reservoir need not be formed by a hollow and blind body that includes only one opening, but may be formed by a hollow cylinder that is open axially at both ends. The cylinder would thus be closed at the proximal end by a first stopper and at the distal end by a second stopper, the volume defined between said two stoppers containing the fluid to be dispensed. When the user actuates the device, the user presses axially on the actuator body so as to slide it axially towards the dispenser orifice, as described above. This causes the second stopper to move inside the reservoir. However, since the fluid is incompressible, the movement of the second stopper thus moves the first stopper towards the needle, which is stationary. The first stopper is thus pierced by the needle and the contents of the reservoir are dispensed through said needle by the second stopper which thus acts as a piston. In this embodiment, the second stopper forms the dispenser means. This embodiment could incorporate a porous insert as described above with reference either to the first embodiment in FIGS. 1 to 3, or to the second embodiment in FIGS. 4 and 5. As described above, at the end of dispensing, any residual fluid that might remain inside the device, in said passage means and/or in said dispenser orifice, is sucked up, at least in part, by said porous insert, preventing access to this trapped volume of residual fluid.

As described above, the invention could also apply to a device of the dual-dose type. In that configuration, the contents of the reservoir would be dispensed in two successive actuations. Document WO 2014/147329 describes an example of a dual-dose device. In such a variant, the porous insert of the first embodiment in FIGS. 1 to 3 would act between the two doses to prevent the residual fluid from being contaminated and then dispensed during the second actuation. Naturally, said porous insert could act equally well in the manner described above to prevent access to any residual fluid trapped after each actuation. A combination of the first and second embodiments would be advantageous, making it possible, with a porous insert arranged around the passage means, to trap any residual fluid after the first actuation, and making it possible, with another porous insert arranged in the bottom of the reservoir, to trap any residual fluid after the second actuation.

Naturally, other variant embodiments may also be envisaged, without going beyond the ambit of the present invention, as defined by the accompanying claims.

The invention claimed is:

1. A fluid dispenser device comprising: a reservoir (10) containing fluid; a dispenser head (20) that is provided with a dispenser orifice (21); dispenser means comprising a stopper for dispensing at least a fraction of said fluid through said dispenser orifice (21); and passage means (40) for connecting said reservoir (10) to said dispenser orifice (21) on actuation of said dispenser means, said device further comprising at least one porous insert (50) that is made out of porous material so as to suck up and to trap, at least in part, residual fluid after actuation; wherein said reservoir (10) includes the stopper (25) that closes said reservoir (10) in leaktight manner before actuation;

wherein said porous insert is arranged, at least in part, around said passage means; and wherein a distal rigid insert is arranged upstream from said porous insert.

2. The device according to claim 1, wherein said passage means (40) include a needle (41) that is adapted to pierce said stopper (25) during actuation.

3. A device according to claim 2, wherein said needle (41) is stationary relative to said dispenser orifice (21).

4. The device according to claim 1, wherein said porous insert (50) is made out of porous hydrophilic polymer.

5. The device according to claim 1, wherein, after actuation, said porous insert (50) extends, at least in part, into said reservoir (10).

6. The device according to claim 1, wherein a proximal rigid insert (60) is arranged downstream from said porous insert (50).

7. The device according to claim 6, wherein said proximal rigid insert (60) defines a spray profile directly upstream from said dispenser orifice (21).

8. The device according to claim 1, wherein said porous insert (50) is arranged axially between said proximal rigid insert (60) and said distal rigid insert (70).

9. The device according to claim 1, wherein said at least one porous insert made out of porous material is configured to suck up by capillarity the residual fluid after actuation.

10. A fluid dispenser device comprising: a reservoir (10) containing fluid; a dispenser head (20) that is provided with a dispenser orifice (21); dispenser means comprising a stopper for dispensing at least a fraction of said fluid through said dispenser orifice (21); and passage means (40) for connecting said reservoir (10) to said dispenser orifice (21) on actuation of said dispenser means, said device further comprising at least one porous insert (50) that is made out of porous material so as to suck up and to trap, at least in part, residual fluid after actuation; wherein said reservoir (10) includes the stopper that closes said reservoir (10) in leaktight manner before actuation;

wherein said porous insert is arranged in said reservoir; and wherein said reservoir (10) contains a second stopper (26) that separates said porous insert (50) from the fluid contained in said reservoir (10).

11. The device according to claim 10, wherein, at the end of actuation, said needle (41) pierces said second stopper (26) so as to connect said porous insert (50) to said passage means (40).

12. The device according to claim 9, wherein said porous insert is made out of porous hydrophilic polymer.

* * * * *